(12) United States Patent
Ura

(10) Patent No.: US 6,234,797 B1
(45) Date of Patent: *May 22, 2001

(54) DENTAL IMPLANT AND METHOD FOR INSTALLING THE SAME

(75) Inventor: Robert S. Ura, Edina, MN (US)

(73) Assignee: Altiva Corporation, Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/416,355

(22) Filed: Oct. 12, 1999

Related U.S. Application Data

(63) Continuation-in-part of application No. 09/175,007, filed on Oct. 19, 1998, now Pat. No. 5,967,783.

(51) Int. Cl.$^7$ ............................................. A61L 8/00
(52) U.S. Cl. ................................................. 433/174
(58) Field of Search .................... 433/174, 221; 606/65, 73

(56) References Cited

U.S. PATENT DOCUMENTS

| | | |
|---|---|---|
| 3,905,109 * | 9/1975 | Cohen et al. .................. 433/174 |
| 4,406,623 | 9/1983 | Grafelman et al. . |
| 4,842,518 | 6/1989 | Linkow et al. . |
| 5,007,835 | 4/1991 | Valen . |
| 5,015,186 | 5/1991 | Detsch . |
| 5,052,930 | 10/1991 | Lodde et al. . |
| 5,087,201 * | 2/1992 | Mondani et al. .................. 433/174 |
| 5,088,926 | 2/1992 | Leng . |
| 5,145,371 | 9/1992 | Jorneus . |
| 5,199,873 * | 4/1993 | Schulte et al. .................. 433/174 |
| 5,209,659 | 5/1993 | Friedman et al. . |
| 5,322,443 | 6/1994 | Beaty . |
| 5,336,225 | 8/1994 | Zang . |
| 5,338,197 | 8/1994 | Kwan . |
| 5,505,736 | 4/1996 | Reimels et al. . |
| 5,522,843 | 6/1996 | Zang . |
| 5,527,183 * | 6/1996 | O'Brien ............................... 433/174 |
| 5,538,428 | 7/1996 | Staubli . |
| 5,544,993 * | 8/1996 | Harle ...................................... 606/73 |
| 5,603,338 | 2/1997 | Beaty . |
| 5,642,996 | 7/1997 | Mochida . |
| 5,643,269 | 7/1997 | Harle . |
| 5,662,476 | 9/1997 | Ingber et al. . |
| 5,692,904 | 12/1997 | Beaty et al. . |
| 5,720,766 | 2/1998 | Zhang et al. . |
| 5,743,914 | 4/1998 | Skiba . |
| 5,967,783 | 10/1999 | Ura . |

FOREIGN PATENT DOCUMENTS 9014801   12/1990  (WO) .

OTHER PUBLICATIONS

Advertising brochure entitled "Biocortical Screw Implant", copyright 2000.
Product Catalog for "Biocortical Screw Implant", copyright 2000.
Price list for "Biocortical Screw Implant", copyright 2000.
Document entitled, "Published Scientific Literature on the Biocortical Screw Implant", undated.

* cited by examiner

Primary Examiner—Todd E. Manahan
(74) Attorney, Agent, or Firm—Dorsey & Whitney LLP

(57) ABSTRACT

A dental implant having an external thread configuration and/or a structure which facilitates a single step dental implant/prosthesis installation or which significantly reduces healing time between surgeries. The invention also relates to a method for installing such a dental implant.

19 Claims, 6 Drawing Sheets

DENTAL IMPLANT AND METHOD FOR INSTALLING THE SAME

This is a continuation-in-part of U.S. application Ser. No. 09/175,007, filed Oct. 19, 1998 now U.S. Pat. No. 5,967,783.

BACKGROUND OF THE INVENTION

1. Field of the Invention

The present invention relates generally to a dental implant, and more particularly to a dental implant with a thread design and structure which provides for dramatically improved loading to thereby facilitate an immediate load implant or an implant with dramatically reduced healing time. The present invention also relates to a method of installing the above identified implant.

2. Description of the Prior Art

Dental implants of various configurations currently exist in the art. These implants are installed into prepared bone sites and function as a device for anchoring a component such as a tooth or dental appliance in the patient's mouth. Examples of currently available dental implants are shown in U.S. Pat. No. 5,062,800 issued to Niznick, U.S. Pat. No. 5,368,160 issued to Leuschen, et al. and U.S. Pat. No. 5,582,299 issued to Laxnaru. Existing dental implant devices commonly include an implant having external threads for installation into a prepared bone site and a hollow interior with internal threads extending from its superior or top end downwardly into the interior of the main body of the implant. Such internal threads are used for connecting an implant mount during the installation process and for connecting a healing cap or a replacement tooth or other prosthesis when the installation is complete. During installation, the implant mount is connected with the implant via a threaded clamp screw. The implant mount interfaces with the implant through a hex connection which enables the implant to be rotated via rotation of the implant mount. It is common for the implant to be provided to the attending surgeon in a pre-mounted position with the implant mount connected to the implant by the clamp screw.

Installation of a dental implant in accordance with current procedures can be summarized as follows. After preparation of the bone site, a dental hand piece with a placement adaptor is positioned onto the implant mount via a hex or other connection. The implant is then positioned in the prepared bone site and installed by rotation of the implant mount, and thus the implant, in a forward or clockwise direction. The hand piece with attached placement adaptor is then removed from the implant mount and an open end wrench or other tool is positioned onto the hex end of the implant mount to remove the same. Because the interface between the threads of a conventional implant and the surrounding bone or tooth tissue is insufficient to resist the compressive forces resulting from normal chewing or biting action, it is necessary to allow the bone or tooth tissue in contact with such threads to heal before a replacement tooth or other prosthesis can be applied. In most cases, this period can be six months or more. Thus, following installation of a conventional implant and removal of the implant mount, a protective cover or healing screw is screwed into the internal threads of the hollow interior for the duration of the required healing time. In some cases the soft tissue surrounding the implant is extended and sutured over the healing screw, while in other cases the top of the implant is substantially flush with the surrounding tissue and the healing screw remains exposed during the healing period.

After the healing period has passed, the surgeon removes the protective screw and installs a healing cap. This healing cap is nonfunctional and remains in place while the tissue heals, generally 4–6 weeks. After this time period, the restoring doctor installs the replacement tooth or other prosthesis. The replacement tooth or other prosthesis commonly includes a mounting stem with external threads to be received by the internal threads of the hollow interior. Several drawbacks exist with respect to the current procedure. The primary drawback is that current procedures require two surgeries at intervals spaced by the required healing time: one surgery to install the implant, and a second surgery to remove the healing screw and install the healing cap and then later, the replacement tooth or prosthesis. The required healing time can be up to six months or longer. With conventional implants, the six month or more waiting time is needed because the external threads of the implant do not efficiently distribute the load and the bone is not strong enough immediately after installation to be fully loaded or to support the implant with a connected replacement tooth or other prosthesis. Thus, with current implants embodying current external designs, a healing period of up to six months or more is required after the first surgery (installation of the implant) to allow the tooth bone to grow around the implant and to heal.

Prior implant designs have existed that allowed a tooth to be placed on the implant immediately. However, these designs utilized osseointegration rather than the current bone implant connection. A further design utilized a threaded implant in combination with a series of tapping instruments to obtain the required compressive force resistance for immediately loading the tooth. Neither of these designs, however, has been widely accepted.

Accordingly, there is a need in the art for an improved dental implant with an improved thread configuration and an improved implant structure which eliminates the second surgery or dramatically reduces the time interval between the first surgery and placement of the final prosthesis.

SUMMARY OF THE INVENTION

In contrast to the prior art, the present invention relates to a dental implant which facilitates elimination of the second surgery to remove the healing cap and apply the prosthesis or which facilitates significant reduction of the time necessary between the first surgery and placement of the final prosthesis. More specifically, the present invention relates to a dental implant structure in which the ratio of the minor to major thread diameters (the core to thread ratio) is decreased, or the ratio of the major to minor thread diameters (the thread to core ratio) is increased. Specifically, these ratios are decreased and increased, respectively, to increase the thread strength of the implant to the point where healing time is eliminated or substantially reduced, thereby facilitating immediate or reduced time loading. The present invention further relates to a dental implant with an improved external thread design which dramatically improves the resistance of the implant to chewing or compressive forces, and thus similarly eliminates or substantially reduces the time period between implant installation and the loading of the implant. Still further, the implant of the present invention is designed to go into, but preferably not through, the cortical plate. Accordingly, the length of the implants of the present invention is preferably less than 20 mm, more preferably no longer than about 15 mm and most preferably about 10–15 mm in length.

To accommodate immediate loading of the implant of the present invention, the two piece abutment and cap screw of prior art implants are eliminated. Accordingly, in the present invention, the implant is provided with a unitary implant in which the threaded portion and the base or abutment portion for supporting the replacement tooth is a single piece structure in which such portions are integrally joined with one another.

One embodiment of the implant of the present invention is to eliminate the hollow interior of the implant and to significantly reduce the core to thread ratio below the standard 0.75. To accommodate the eliminated interior an outwardly extending top or prosthesis receiving post is provided above the neck of the implant to receive the replacement tooth or other prosthesis. It has been found that the reduction in the core to thread ratio results in an unexpectedly increased resistance to compressive forces such as chewing or biting to thereby facilitate immediate loading of the implant.

A further embodiment of the present invention includes providing the implant with an improved external thread design which includes first and second helical threads which are interleaved with one another and which exhibit different outside or major diameters. Preferably at least one of these helical threads is provided with a thread configuration in which the flat or the flatter thread side surface faces toward the distal or non-head end of the implant.

A still further embodiment of the present invention is to provide an implant less than 20 mm in length with the thread design described above.

Accordingly, an object of the present invention is to provide a dental implant which can be fully installed, together with the replacement tooth or other prosthesis, in a single surgery.

Another object of the present invention is to provide a dental implant which eliminates the hollow interior for attaching the prosthesis.

A further object of the present invention is to provide an immediate load dental implant to be installed into, but preferably not through, the cortical plate, thereby providing an implant of preferably less than 20 mm.

A still further object of the present invention is to provide a dental implant with a reduced core to thread ratio and more specifically, a core to thread ratio of no greater than 0.70.

A still further object of the present invention is to provide, independently or in combination with an implant of reduced core to thread ratio and/or an implant with a length of less than 20 mm, a unitary implant having an integral threaded portion and tooth supporting portions.

A still further object of the present intention is to provide a dental implant with an improved external thread configuration to facilitate immediate loading to reduce the interval between first and second surgeries.

A still further object of the present invention is to provide a dental implant structure by which the thread to core ratio can be significantly increased to a ratio of 1.40 or greater.

These and other objects of the present invention will become apparent with reference to the drawings, the description of the preferred embodiment and the appended claims.

DESCRIPTION OF THE PREFERRED EMBODIMENT

The present invention relates to improvements in a dental implant. In general, a dental implant provides support for a replacement tooth or other prosthesis and thus is anchored into a tooth root, bone or other tissue. The dental implant provides support for such replacement tooth or prosthesis at its proximal or superior end. A dental implant does not function to secure two or more pieces of tissue, bones or other elements together as in conventional bone screws, nor does it function to provide any significant resistance to pulling out force as in conventional tissue or bone screws.

Figure 1:
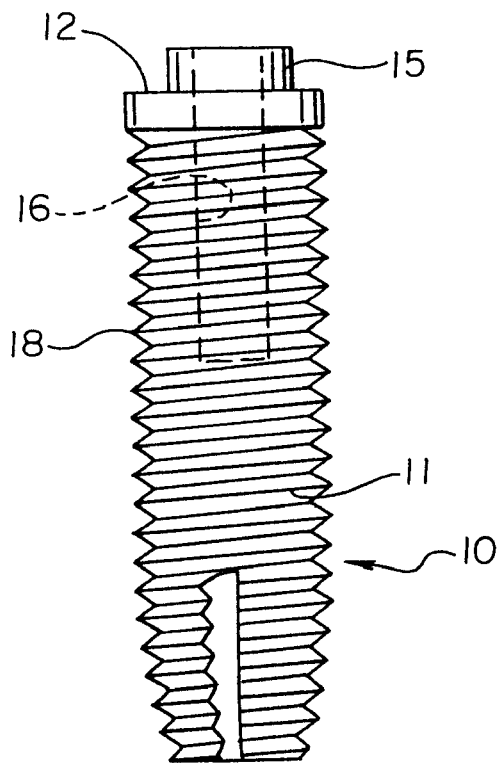
FIG. 1 is a side view, partially in section, of a conventional dental implant.
Figure 2:
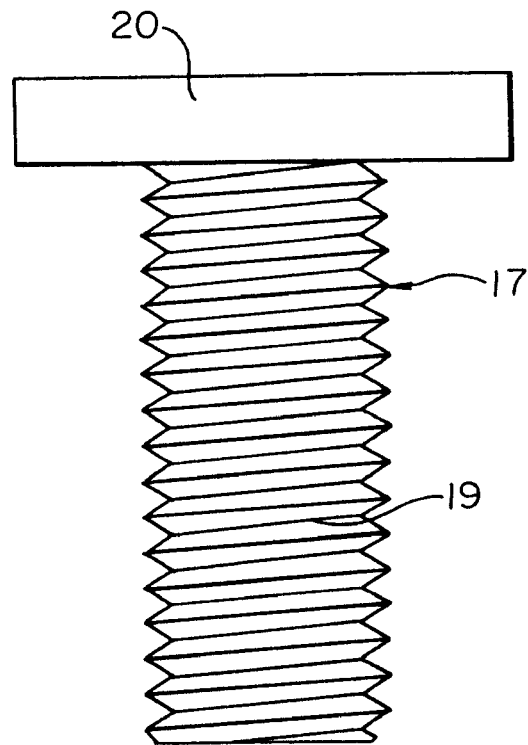
FIG. 2 is an elevational side view of a conventional healing screw for use with the dental implant of FIG. 1.
Figure 3:
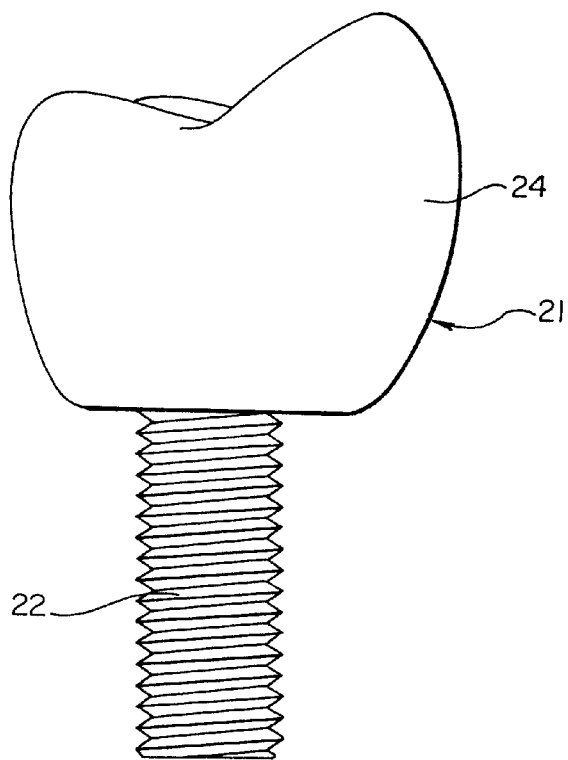
FIG. 3 is an elevational side view of a replacement tooth for use with the dental implant of FIG. 1.

Reference is first made to FIGS. 1, 2, and 3 showing a conventional dental implant and related structures known in the art. Specifically, FIG. 1 illustrates a conventional dental implant 10 having a main body portion 11, a proximal or superior end 12 and a distal or inferior end 14. The proximal end 12 is provided with a conventional hex configuration 15 to enable the implant to be rotated and installed into a pre-drilled hole in a tooth root or bone. The dental implant of FIG. 1 is provided with a hollow interior 16 which extends from the proximal end 12 into the main portion 11 of the implant for a substantial distance toward the distal end 14. This hollow interior 16 is provided with internal threads. The exterior of the implant 10 is provided with threads 18 for securement to a tooth structure.

Conventional dental implants have a core to thread ratio greater than 0.70 with the standard being about 0.75 or greater. This translates into a thread to core ratio of less than about 1.40, with the standard being about 1.20 or less. The core to thread ratio is the ratio between the dimension at the innermost edge of the thread (the minor diameter) to the dimension at the outermost edge of the thread, while the thread to core ratio is the ratio of the major diameter to the minor diameter.

FIGS. 2 and 3 illustrate elements designed for use with the conventional dental implant of FIG. 1. Specifically, FIG. 2 illustrates a healing screw 17 having a proximal or head end 20 and an elongated stem portion 19 extending from the head 20 toward a distal end. The stem portion 19 is provided with external threads designed to be received by the internal threads of the hollow interior 16 (FIG. 1) and is substantially smaller in diameter than the proximal end 20. The healing cap 17 is conventionally screwed into the hollow interior 16 of the implant 10 after installation of the implant and during the healing period for the surrounding bone or tooth tissue.

FIG. 3 illustrates a conventional replacement tooth 21 having an elongated externally threaded stem 22 at its distal end and a replacement tooth portion 24 at its proximal end. The external threads of the stem 22 are designed to mate with the internal threads of the interior portion 16. The replacement tooth 21 is installed into the implant 10 of FIG. 1 after the necessary healing period has elapsed and the healing cap 17 (FIG. 2) has been removed.

General reference is next made to FIGS. 4–7 showing a first embodiment of a dental implant 25 in accordance with the present invention. The dental implant 25 includes a main body portion 26 with a proximal or superior end 28 and a distal or inferior end 29. As illustrated best in FIGS. 4 and 6, the distal end 29 is provided with a plurality of cutting edges 32 to provide the implant with self tapping capabilities. The cutting edges 32 or other self-tapping structures as applied to dental implants are well known in the art and such structures are incorporated herein by reference. In the preferred embodiment, the distal end 29 of the implant 25 is also provided with a through-hole 34 for later bone growth, if desired. Such hole 34, however, is not necessary to achieve the other benefits of the implant 25.

Figure 4:
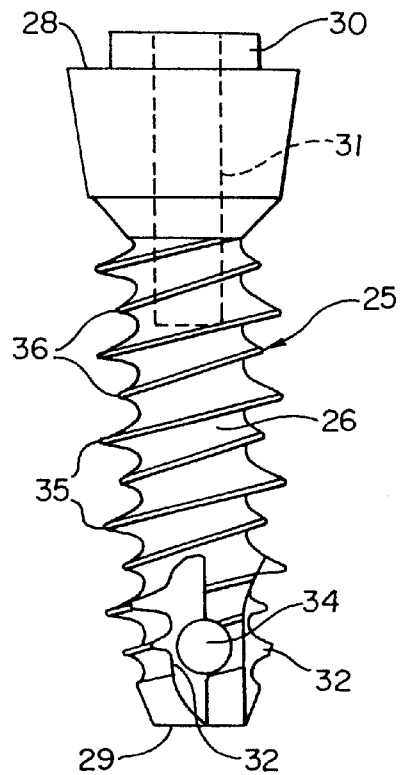
FIG. 4 is a side view, partially in section, of one embodiment of the dental implant in accordance with the present invention.
Figure 7:
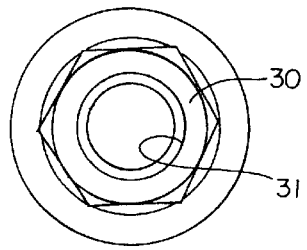
FIG. 7 is an elevational top view from the proximal or head end of the dental implant of FIG. 4.

As shown in FIGS. 4 and 7, the proximal end 28 is provided with a rotation head in the form of a hex end or portion 30 for engagement by a hand piece or other tool or adaptor for the purpose of rotating the implant 25 during installation. A hollow interior 31 extends from the proximal end 28 into the main portion 26 of the implant 25 for a substantial distance toward the distal end 29. The hollow interior 31 is provided with internal threads to receive a conventional healing cap or replacement tooth such as as shown in FIGS. 2 and 3, respectively, or any other prosthesis or attachment intended for use with dental implants. In this embodiment, the diameter of the hollow interior 31 is reduced relative to that of conventional implants to accommodate the reduced core to thread ratio.

The exterior of the main body of the implant 25 as shown in FIG. 4 is provided with a plurality of external threads comprising a first series of helical threads 35 extending from the distal end 29 substantially to the proximal end 28 and a second series of helical threads 36 interleaved between the first series of helical threads 35 and also extending from the distal end 29 substantially to the proximal end 28. In the preferred embodiment, the helical threads 35 and 36 have first and second outer diametrical dimensions which are different from one another. As shown generally in FIG. 4 and more specifically in FIG. 5, the outer or major diameter of the first series of helical threads 35 is greater than the outer or major diameter of the second series of helical threads 36.

Figure 5:
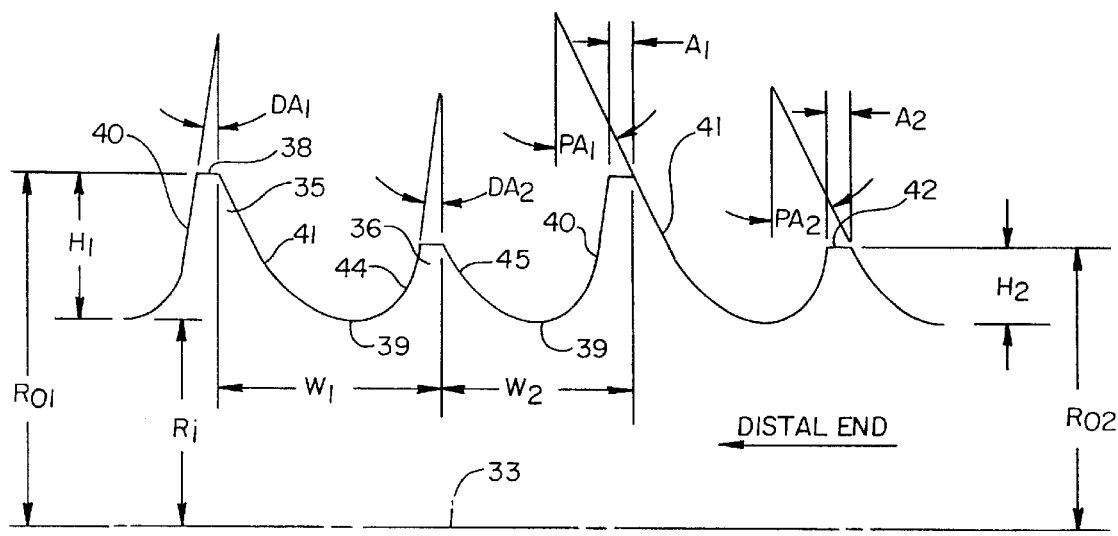
FIG. 5 is an enlarged sectional view of the thread configuration of the implant of the embodiment shown in FIG. 4.
Figure 6:
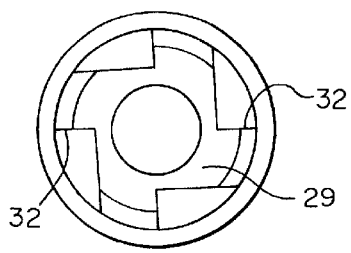
FIG. 6 is an elevational bottom view from the distal end of the dental implant of FIG. 4.

With reference to FIG. 5, each of the first series of helical threads 35 includes an outer edge 38 extending helically around the implant 25 and defining the thread diameter or major diameter of the threads 35. The specific size of this outer or major diameter, which is twice the radius "$R_{O1}$" shown in FIG. 5 as the distance between the edge 38 and the implant centerline 33, will depend of the particular size of the implant. Conventional implants normally include implants with diameters of 3 mm to 6 mm, with most standard implants being 4 mm or 5 mm. Implants are conventionally provided in lengths from 10 mm to 15 mm and specifically in lengths of 10 mm, 11.5 mm, 13 mm and 15 mm.

The helical threads 35 also include an inner edge 39. The inner edge 39 defines the core diameter or minor diameter of the thread 35 which, as shown in FIG. 5, is twice the distance "$R_i$" between the edge 39 and the centerline 33. The core diameter 39 defines the innermost portion of the thread 35. Like the outer edge 38, the inner edge 39 of the thread extends helically around the implant 25. The core to thread ratio or the minor to major diameter ratio of thread 35 is determined by comparing the minor diameter defined by twice the distance "$R_i$" to the major diameter defined by twice the distance "$R_{O1}$". Preferably this ratio $R_i/R_{O1}$ is about 0.70 or less and more preferably about 0.60 or less. The range of core to thread ratios for implants in accordance with the present invention is preferably 0.40 to 0.70, more preferably 0.45 to 0.65 and most preferably 0.50 to 0.60. These ratios are based on a major diameter of 4 mm and a minor diameter of about 2.25 mm for a 4 mm implant, and a major diameter of 5 mm and a minor diameter of about 3 mm for a 5 mm implant.

With these core to thread ratios, it has unexpectedly been found that the resistance of the implant to compressive forces is dramatically increased. This increase is significantly greater than what one would expect by comparing the relative thread surface areas of the implant of the present invention with those of conventional implants with a standard core to thread ratio of about 0.75.

In a preferred embodiment, the outer edge 38 terminates in a flat surface generally parallel to the longitudinal axis of the implant as shown. Although it can, if desired, terminate substantially at a point, it is preferred that the outer edge 38 terminate in a flat portion as shown having a dimension "$A_1$" of less than about 0.2 mm and more preferably between about 0.03 and 0.15 mm.

The particular height $H_1$ of the thread 35 defined by the distance between the outer edge 38 and the inner edge 39 will vary with the particular size of the implant, the amount of torque desired to install the implant and the compressive force resistance desired.

The thread 35 also includes a pair of side surfaces extending helically from the distal end 29 of the implant to the proximal end 28. These side surfaces include a distal or distal facing surface 40 and a proximal or proximal facing surface 41. As shown best in FIG. 5, these surfaces 40 and 41 form angles $DA_1$ and $PA_1$, respectively, with a line extending perpendicular to the longitudinal or center axis 33 of the implant. Although these two angles $DA_1$ and $PA_1$ can be the same, it is preferred that the angle $DA_1$ be smaller than the angle $PA_1$ (or that the angle $PA_1$ be larger than the angle $DA_1$). More specifically, it is preferred that the angle $DA_1$ be less than about 45°, more preferably less than about 25°, and most preferably less than about 10°. In contrast, it is preferred that the angle $PA_1$ be between about 45 and 5°, more preferably between about 40 and 10°, and most preferably between about 35 and 20°. With this structure, it is preferred that the surface 40, which comprises the flatter surface or smaller angle face the distal end of the implant as shown.

The thread design 36 is similar to that of the thread 35 except that its outer or major diameter defined by twice the distance "$R_{o2}$" between the outer edge 42 and the centerline 33 is less than the major diameter of the thread 35. Similar to the thread 35, the inner dimension of the thread 36 is defined by the inner edge 39. The core to thread ratio, or minor to major diameter ratio, of the thread 36 is defined as the ratio of its minor diameter (twice the distance "$R_i$") to its major diameter (twice the distance "$R_{o2}$"). This core to thread ratio is expected to be greater than the core to thread ratio of the thread 35 since the denominator of the ratio is less. However, even this ratio is preferably less than the standard ratio of about 0.75. It is contemplated, however, that the core to thread ratio of the smaller thread in a thread pattern of multiple thread diameters could be greater than the standard core to thread ratio of 0.75 without deviating from the present invention.

In determining core to thread ratio in a multiple thread diameter pattern in accordance with the present invention, the major diameter of the largest thread is used. Thus, in the embodiment of FIGS. 4 and 8, the preferred values of the core to thread ratio as set forth above with respect to the thread 35 (the largest thread) are applicable.

Similar to the thread 35, the outer edge 42 of the thread 36 is provided with a flat portion extending helically around the implant. Although this outer portion 42 can terminate at a point, it preferably terminates at a flat portion with a dimension $A_2$ of less than about 0.1 mm and more preferably between about 0.3 and 0.1 mm.

Also, similar to thread 35, the second helical thread 36 includes a pair of sides extending helically along the length of the implant. Specifically, these sides include a distal or distal facing side 44 and a proximal or proximal facing side 45. These sides 44 and 45 form angles $DA_2$ and $PA_2$ with a line extending perpendicular to the longitudinal or center axis 33 of the implant, respectively. Although these angles can be the same, it is preferred for the angle $DA_2$ of the distal side 44 to be smaller than the angle $PA_2$ of the proximal side 45 (or the angle $PA_2$ to be larger than the angle $DA_2$). Preferably the angle $DA_2$ of the distal side 44 is less than 45°, more preferably less than about 25° and most preferably less than about 10°. The angle $PA_2$ of the proximal side 45 is preferably between about 45 and 5°, and more preferably between about 35 and 10°.

The distance between the threads 35 and 36 measured from the top outer edge of the thread 35 to the top outer edge of the thread 36 is defined by the distance $W_1$, while the distance between the threads 36 and 35 measured from the top outer edge of the thread 36 to the top outer edge of the thread 35 is defined by the distance $W_2$. These distances relate to the pitch of the threads or the number of threads per unit length. Preferably, the distances $W_1$, and $W_2$ are such as to provide a pitch for the threads 35 of about 8–20 threads per inch and a similar pitch for the threads 36 of about 8–20 threads per inch. More preferably, the thread pitch should result in 10–18 threads per inch and most preferably about 12 threads per inch. Although the pitch of the threads 35 and 36 is preferably constant throughout the length of the implant, the pitch can be designed to vary, if desired.

In the preferred embodiment, a 13 mm implant has about 4 to 10 turns of the thread 35. More preferably, a 13 mm implant has about 6 to 8 turns of the thread 35. This translates to a thread 35 density pitch of about 12 to 16 threads per inch.

Although the implant of the present invention can be of various lengths, it is preferably of a length that will penetrate the cortical plate, but preferably not go through it. Thus, the preferred implant length in accordance with the present invention is less than 20 mm. More preferably, the length is no greater than 15 mm, and most preferably the length is about 10 to 15 mm. For purposes of the present invention, the length of the implant is that portion comprised of the threads.

Figure 8:
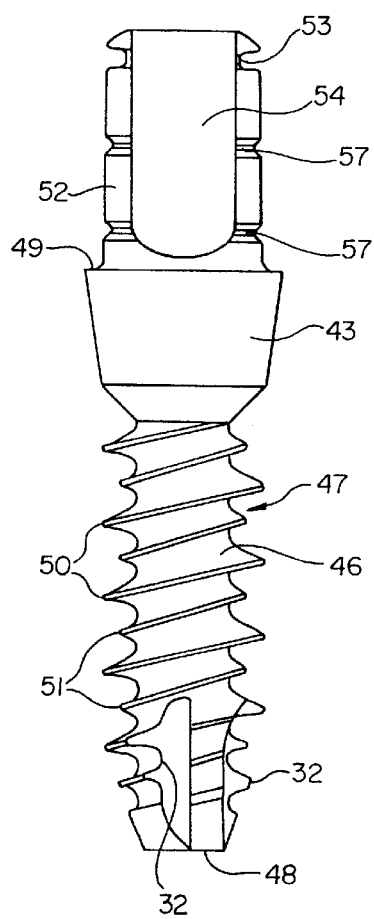
FIG. 8 is a side view, partially in section, of a second embodiment of the dental implant in accordance with the present invention.
Figure 9:
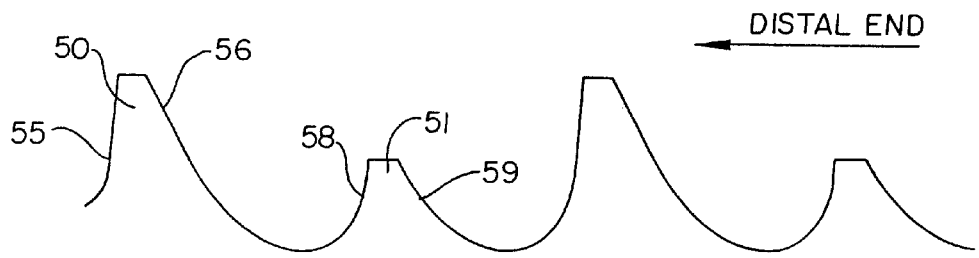
FIG. 9 is an enlarged view of the thread configuration of the embodiment of the dental implant as shown in FIG. 8.
Figure 10:
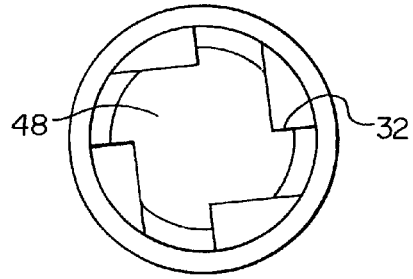
FIG. 10 is an elevational bottom view from the distal end of the dental implant of FIG. 8.
Figure 11:
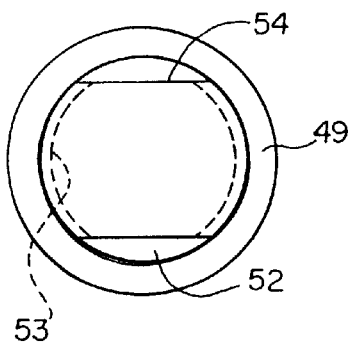
FIG. 11 is an elevational top view from the proximal or head end of the dental implant of FIG. 8.

Reference is next made to FIGS. 8, 9, 10 and 11 illustrating a second embodiment of a dental implant 47 of the present invention. Specifically, the embodiment of the FIG. 8 includes a main implant portion 46 having first and second helical threads 50 and 51, respectively, extending from the distal end 48 toward the proximal end 49. The main body portion 46 and threads 50 and 51 of the embodiment of FIG. 8 are substantially the same as that of the embodiment of FIG. 4. Accordingly, the elevational distal end view of FIG. 10 of the embodiment of FIG. 8 is substantially the same as the distal end view of FIG. 6. The enlarged thread configuration illustrated in FIG. 9 is also similar to that shown in FIG. 5 with respect to the embodiment of FIG. 4. Specifically, the first and second helical threads 50 and 51 of the embodiment of FIG. 8 extend helically along a substantial length of the implant and are interleaved between each other. Further, although not specifically described, the core to thread ratios of the threads 50 and 51 and their respective configurations and dimensions are similar to those described and shown above with respect to FIG. 5. Further, each of the threads 50 and 51 include distal or distal facing sides 55 and 58, respectively, and proximal or proximal facing sides 56 and 59, respectively. The angles which these sides form with a line extending perpendicular to the longitudinal axis or center line of the implant is similar to that disclosed with reference to FIG. 5.

The embodiment of FIG. 8 differs from that of FIG. 4 in that an extended neck 43 is provided between the threaded portion and the proximal end 49, a head or prosthesis receiving post 52 is provided to the proximal end 49 of the implant and the hollowed out interior portion 31 of the embodiment of FIG. 4 is eliminated. Further, the proximal end of the head or post 52 is provided with a structure 54 for rotating the implant 47 during installation. In the preferred embodiment, this structure 54 comprises a pair of flats on opposite sides of the post 52. The structure 54 is designed to mate with a hand piece or other tool or adaptor. However, this structure can be any structure which enables the implant to be rotated. It is also contemplated that a portion of the head or post 52 can be provided with a conventional hex end to receive an appropriate tool for rotation.

As shown best in FIG. 8, the head 52 includes a circumferential groove 53 near its upper end. This groove is intended to receive a rubber loop to assist in installation of the implant. A plurality of grooves 57 are also provided for use when constructing impressions or temporaries.

Figure 15:
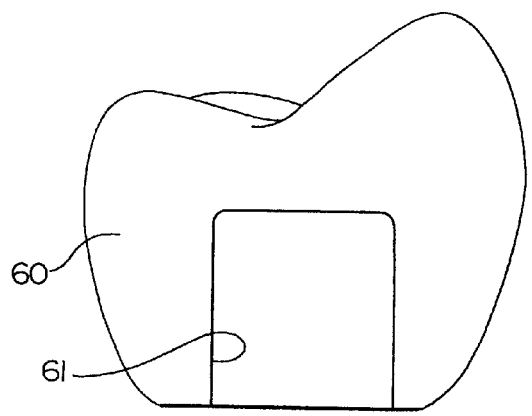
FIG. 15 is an elevational side view, partially in section, of a replacement tooth for use with the implants of FIGS. 8, 12 and 13.

It is contemplated that with the embodiment of FIG. 8, a replacement tooth or other prosthesis such as that illustrated in FIG. 15 would be connected to the post 52. As shown in FIG. 15, the replacement tooth includes a conventional tooth exterior 60 and an interior conforming substantially to the exterior figuration of the post 52 and portion 54 of FIG. 8. It is contemplated that with the embodiment of FIG. 8, the replacement tooth of FIG. 15 would be secured to the post 52 through an appropriate adhesive. The neck 43 can be of varying heights depending on the nature of the tissue and the particular prosthesis used. Preferably, the height of the neck 43 is between about 0.5 and 8 mm and most preferably between about 1 and 5 mm.

Figure 12:
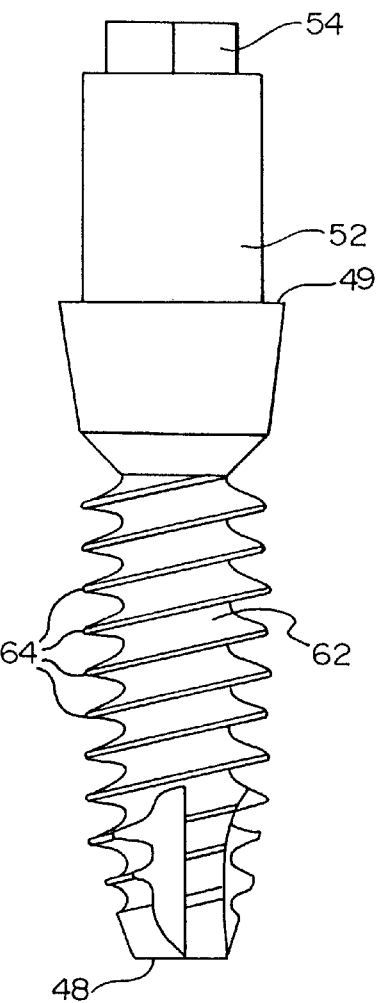
FIG. 12 is a side view, partially in section, of a third embodiment similar to that of FIG. 8, but with a modified thread design.

The embodiment shown in FIG. 12 is an embodiment similar to that of FIG. 8 except that the threads 64 of the implant of FIG. 12 are of the same diameter and are symmetrical. The core to thread ratio of the threads 64, however, are substantially the same as that of the embodiment of FIG. 4. Specifically, the core to thread ratios are preferably 0.70 or less and more preferably 0.60 or less. The preferred ranges of such ratios are 0.40 to 0.70, with more preferred and most preferred ratios being 0.45 to 0.65 and 0.50 to 0.60, respectively. FIG. 12 also includes a modified prosthesis receiving post comprising the post 63 extending outwardly from the neck 43 and a hexagonal end 54 to facilitate rotation of the implant.

Figure 13:
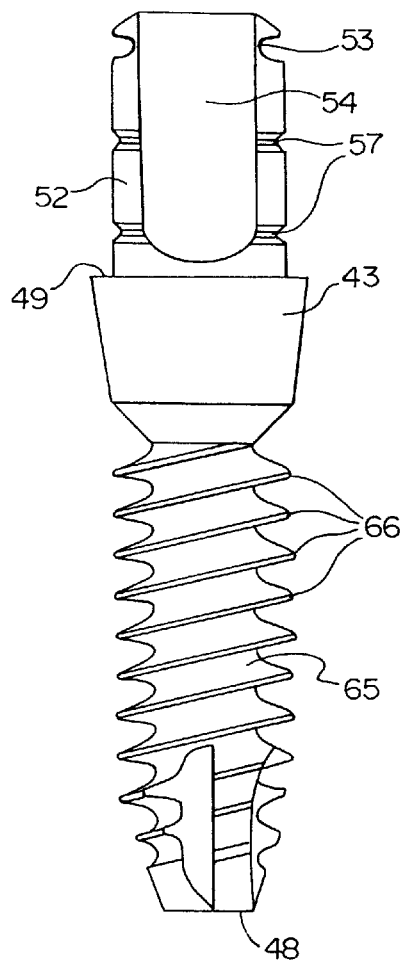
FIG. 13 is a side view, partially in section, of a fourth embodiment of the dental implant of the present invention, which view is similar to that of FIG. 8, but with a further modified thread design.
Figure 14:
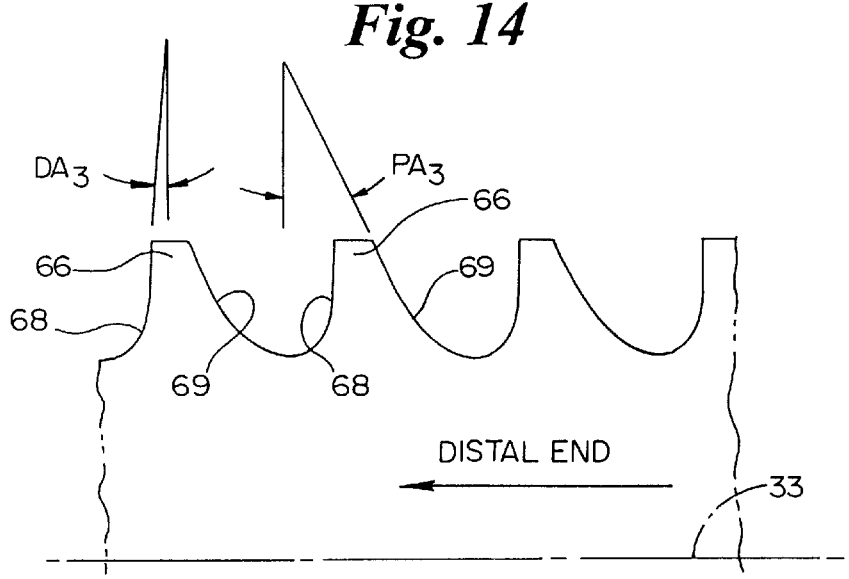
FIG. 14 is an enlarged view of the thread pattern of the dental implant embodiment of FIG. 13.

The embodiment of FIG. 13 is similar to that of the embodiment of FIG. 12 in that the threads 66 are of equal outer diameter, but is dissimilar to that of FIG. 12 in that the threads are not symmetrical. The details of this thread configuration are shown in FIG. 14. As shown in FIG. 14, the distal or distal facing side 68 of the threads 66 forms an angle $DA_3$ with a line perpendicular to the longitudinal axis or center line 33 of the implant, while the proximal or proximal facing side 69 of the threads 66 forms an angle $PA_3$. In the embodiment of FIGS. 13 and 14, the angle $DA_3$ is less than the angle $PA_3$ (or the angle $PA_3$ is greater than the angle $DA_3$), with the preferred values of those angles being similar to those described above with respect to FIG. 5.

Figure 17:
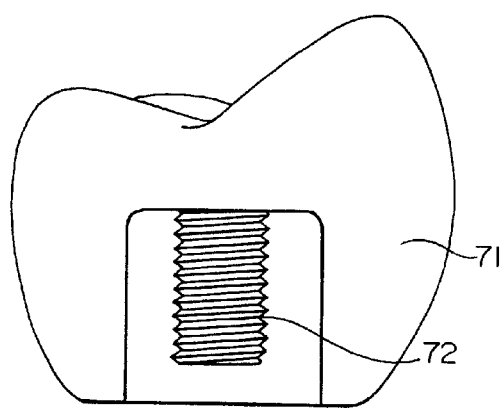
FIG. 17 is a modified replacement tooth for use with the prosthesis receiving post design of FIG. 16.
Figure 16:
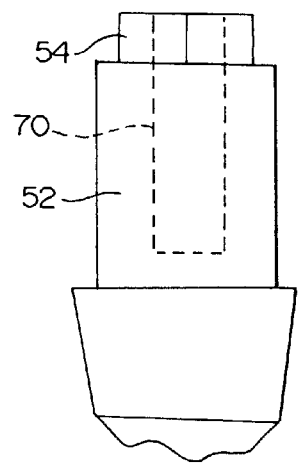
FIG. 16 is a modified prosthesis receiving post for the embodiments of FIGS. 8, 12 and 13.

FIG. 16 illustrates an alternate prosthesis receiving post for the implant embodiments of FIGS. 8, 12 and 13. In the embodiment of FIG. 16, the head or post portion 52 is provided with an internal recess 70. This recess 70 is provided with internal threads which are intended to receive external threads from a replacement tooth such as that illustrated in FIG. 17. In FIG. 17, the replacement tooth includes a main replacement tooth portion 71 and an elongated stem portion 72 having external threads matching the internal threads of the internal portion 70 of FIG. 16. As shown, the stem portion 72 is positioned entirely within the tooth portion 71. To install the replacement tooth of FIG. 17 on the implant of FIG. 16, the stem 72 is positioned into the interior portion 70 and rotated until tight.

Having described the detailed structure of the preferred embodiment of the present invention, the use of the dental implant and the method aspect of the present invention can be understood best as follows: First, a dental implant is provided which includes a proximal end, a distal end and an externally threaded shaft. The shaft preferably includes a core to thread ratio as specified above. The shaft further includes first and second helical threads which are interleaved with one another and embody first and second thread diameters, with one of the thread diameters being different than the other. The implant also preferably includes a prosthesis receiving post integrally positioned at the proximal end of the implant and extending outwardly from the proximal end to receive a prosthesis. The method further includes drilling or boring a hole into a tooth root or bone at a desired location and then inserting the distal end of the implant into the hole and rotating the dental implant to a desired degree of installation. Preferably, the implant is not installed through the cortical plate. Finally, a replacement tooth or other prosthesis is mounted or attached to the prosthesis receiving post either via a threaded connection, adhesives, or the like. This installation of the replacement tooth or prosthesis is preferably performed immediately. Thus, the preferred method is a single surgery method in which both the installation of the implant and the installation of the prosthesis are completed in a single office visit.

Although the description of the preferred embodiment has been quite specific, it is contemplated that various modifications could be made without deviating from the spirit of the present invention. Accordingly, it is intended that the scope of the present invention be dictated by the appended claims rather than by description of the preferred embodiment.

What is claimed is:

1. A dental implant comprising:
an elongated externally threaded shaft having a longitudinal axis;
a distal end;
a proximal end;
a rotation head at said proximal end; and
said threaded shaft including two or more helical threads extending from said distal end substantially to said proximal end, at least one of said helical threads comprising an inner edge definng a thread minor diameter, an outer edge defining a thread major diameter, a proximal surface extending between said inner edge and said outer edge and facing said proximal end and a distal surface extending between said inner edge and said outer edge and facing said distal end, the ratio of said thread minor diameter to said thread major diameter defining a core to thread ratio, with the core to thread ratio of said at least one thread being about 0.45 to about 0.70.

2. The dental implant of claim 1 wherein said core to thread ratio is about 0.50 to 0.60.

3. The dental implant of claim 1 wherein said threaded shaft includes first and second helical threads interleaved with one another and having different diameters.

4. The dental implant of claim 3 wherein said first thread includes a first proximal facing surface facing said proximal end and a first distal surface facing said distal end, wherein said first proximal facing surface forms a first acute proximal angle relative to a line perpendicular to said longitudinal axis, wherein said first distal facing surface forms a first acute distal angle relative to a line perpendicular to said longitudinal axis and wherein said first acute proximal angle is greater than said first acute distal angle.

5. The dental implant of claim 4 wherein said first thread diameter is greater than said second thread diamter.

6. The dental implant of claim 5 wherein said first acute distal angle is less than 25°.

7. The dental implant of claim 1 including a replacement tooth receiving portion extending from said proximal end and being integrally formed with said threaded shaft.

8. The dental implant of claim 7 wherein said threaded shaft is free of any internal threaded portion.

9. The dental implant of claim 1 including an internally threaded bore extending into said shaft from said proximal end and along said longitudinal axis.

10. The dental implant of claim 3 wherein said first and second threads includes first and second proximal facing surfaces forming first and second acute proximal angles, respectfully, relative to a line perpendicular to said longitudinal axis, wherein said first and second threads include first and second distal facing surfaces forming first and second acute distal angles, respectfully, relative to a line perpendicular to said longitudinal axis, and wherein said first and second acute proximal angles are greater than their corresponding first and second acute distal angles.

11. The dental implant of claim 1 including an integral dental prosthesis receiving post positioned at said proximal end and extending outwardly therefrom.

12. The dental implant of claim 11 wherein said shaft is free of any internal bore.

13. The dental implant of claim 1 in combination with a dental prosthesis.

14. A method of installing a dental implant and appliance comprising the steps of:
providing a dental implant having a proximal end, a distal end and an externally threaded shaft, said shaft including at least two helical threads extending from said distal end substantially to said proximal end, at least one of said helical threads comprising an inner edge defining a thread minor diameter, an outer edge defining a thread major diameter, a proximal surface extending between said inner edge and said outer edge and facing said proximal end and a distal surface extending between said inner edge and said outer edge and facing said distal end, the ratio of said thread minor diameter to said thread major diameter defining a core to thread ratio, said core to thread ratio of said one helical thread being about 0.45 to about 0.70 and said implant further including a prosthesis receiving member positioned at said proximal end;
drilling a hole into a tooth root or bone at a desired location;
inserting said distal end into said hole and rotating said dental implant to a desired degree of installation; and
attaching a prosthesis to said prosthesis receiving member.

15. The method of claim 14 wherein said prosthesis is attached to said receiving member immediately after said insertion step.

16. A dental implant, comprising:
a proximal end;
a distal end;
a rotation member at said proximal end;
an elongated externally threaded shaft having at least one sharp bladed thread and a longitudinal axis wherein said at least one thread comprises an inner edge defining a thread minor diameter and an outer edge defining a thread major diameter with the ratio of said thread minor diameter to said thread major diameter defining a core to thread ratio and wherein said thread has a core to thread ratio of about 0.45 to about 0.70 and extends from said distal end substantially to said proximal end; and
a prosthesis receiving member postioned at said proximal end.

17. The dental implant of claim 16 wherein said at least one thread includes a proximal facing surface forming a proximal angle with a line perpendicular to said longitudinal axis and a distal facing surface forming a distal angle with a line perpendicular to said longitudinal axis and wherein said proximal angle is greater than said distal angle.

18. The dental implant of claim 16 being lesss than 20 mm in length.

19. A method of installing a dental implant and appliance comprising the steps of:
providing a dental implant having a proximal end, a distal end and an externally threaded shaft, said shaft including at least one helical thread extending from said distal end substantially to said proximal end, said at least one helical thread comprising an inner edge defining a thread minor diameter, an outer edge defining a thread major diameter, a proximal surface extending between said inner edge and said outer edge and facing said proximal end and a distal surface extending between said inner edge and said outer edge and facing said distal end, the ratio of said thread minor diameter to said thread major diameter defining a core to thread ratio, said core to thread ratio of said thread being about 0.45 to about 0.70 and said implant further including a prosthesis receiving member positioned at said proximal end;
drilling a hole into a tooth root or bone at a desired location;
inserting said distal end into said hole and rotating said dental implant to a desired degree of installation; and
attaching a prosthesis to said prosthesis receiving member.

* * * * *